US 10,178,957 B2

(12) United States Patent
Schmeitz et al.

(10) Patent No.: US 10,178,957 B2
(45) Date of Patent: Jan. 15, 2019

(54) DEVICE AND METHOD FOR VITAL SIGN MEASUREMENT OF A PERSON

(75) Inventors: Harold Agnes Wilhelmus Schmeitz, Eindhoven (NL); Marek Janusz Bartula, Eindhoven (NL); Tim Johannes Willem Tijs, Eindhoven (NL); Gijs Antonius Franciscus Van Elswijk, Eindhoven (NL); Murray Fulton Gillies, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 686 days.

(21) Appl. No.: 14/008,094

(22) PCT Filed: Apr. 16, 2012

(86) PCT No.: PCT/IB2012/051875
§ 371 (c)(1),
(2), (4) Date: Sep. 27, 2013

(87) PCT Pub. No.: WO2012/143842
PCT Pub. Date: Oct. 26, 2012

(65) Prior Publication Data
US 2014/0031696 A1 Jan. 30, 2014

(30) Foreign Application Priority Data
Apr. 21, 2011 (EP) .................................... 11163329

(51) Int. Cl.
*A61B 5/08* (2006.01)
*G06F 19/00* (2018.01)
(Continued)

(52) U.S. Cl.
CPC .......... *A61B 5/0205* (2013.01); *A61B 5/0077* (2013.01); *A61B 5/02416* (2013.01);
(Continued)

(58) Field of Classification Search
None
See application file for complete search history.

(56) References Cited

U.S. PATENT DOCUMENTS

| 6,705,990 B1 | 3/2004 | Gallant et al. |
| 2004/0082874 A1 | 4/2004 | Aoki et al. |

(Continued)

FOREIGN PATENT DOCUMENTS

| CN | 101810472 A | 8/2010 |
| CN | 101828908 A | 9/2010 |

(Continued)

OTHER PUBLICATIONS

Cennini et al. "Heart rate monitoring via remote photoplethysmography with motion artifacts reduction", Optics Express, vol. 18, No. 5, Feb, 2010.*

(Continued)

Primary Examiner — Katherine Fernandez
Assistant Examiner — Marjan Saboktakin

(57) ABSTRACT

The present invention relates to a device (1) for vital sign measurement of a person (2), comprising presentation means (10) for presenting a person (2) with a visual theme (20), illumination means (11) for illuminating an illumination area (3), in which said person (2) is located, whose vital signs shall be measured, optical measurement means (12) for optically detecting optical detection signals (23) from said illumination area (3), evaluation means (13) for evaluating said optical detection signals (23) and deriving a vital sign information (24) from them, and control means (14) for controlling said illumination means (11) to illuminate said illumination area (3) allowing the detection of optical detection signals (23), from which a vital sign information (24) can be derived despite changes of the visual theme (20).

15 Claims, 1 Drawing Sheet

(51) Int. Cl.
  *A61B 5/11* (2006.01)
  *A61B 5/0205* (2006.01)
  *A61B 5/00* (2006.01)
  *A61B 5/024* (2006.01)

(52) U.S. Cl.
  CPC ............ *A61B 5/0816* (2013.01); *G06F 19/00* (2013.01); *A61B 5/1128* (2013.01); *A61B 2505/07* (2013.01)

(56) References Cited

U.S. PATENT DOCUMENTS

| | | | |
|---|---|---|---|
| 2007/0100214 A1* | 5/2007 | Steinert | A61H 1/00 600/300 |
| 2008/0214903 A1 | 9/2008 | Orbach | |
| 2008/0292151 A1* | 11/2008 | Kurtz | A61B 3/10 382/128 |
| 2009/0043210 A1 | 2/2009 | Kitoh et al. | |
| 2009/0093688 A1 | 4/2009 | Mathur | |
| 2009/0299675 A1 | 12/2009 | Isaacson et al. | |
| 2011/0034811 A1 | 2/2011 | Naujokat et al. | |

FOREIGN PATENT DOCUMENTS

| | | |
|---|---|---|
| CN | 201578231 A | 9/2010 |
| CN | 201641989 U | 11/2010 |
| EP | 2425768 B1 | 2/2015 |
| JP | 63212330 A | 9/1998 |
| JP | 2002175582 A | 6/2002 |
| JP | 2008532587 A | 8/2008 |
| JP | 2008281239 A | 11/2008 |
| JP | 2010104455 A | 5/2010 |
| JP | 2010231663 A | 10/2010 |
| WO | 2007043328 A1 | 4/2007 |
| WO | 2009153700 A1 | 12/2009 |
| WO | WO 2009153700 A1 * 12/2009 ......... A61B 5/14551 |
| WO | 2010125705 A1 | 11/2010 |
| WO | 20110211128 A2 | 2/2011 |

OTHER PUBLICATIONS

Nakajima et al. "Monitoring of heart and respiratory rates by photoplethysmography using a digital filtering technique", Med. Eng. Phys. vol. 18, No. 5, pp. 365-372, 1996.*

Poh et al. "Non-contact, automated cardiac pulse measurements using video imaging and blind source separation", Optical Express, May 2010.*

Tan et al. "Real-time vision based respiration monitoring system", IEEE, 2010.*

Wim Verkruysse et al, "Remote plethysmographic imaging using ambient light", Optics Express, vol. 16, No. 26, pp. 1-16, Dec. 2008.

* cited by examiner

DEVICE AND METHOD FOR VITAL SIGN MEASUREMENT OF A PERSON

CROSS-REFERENCE TO PRIOR APPLICATIONS

This application is the U.S. National Phase application under 35 U.S.C. § 371 of International Application No. PCT/IB2012/051875, filed on Apr. 16, 2012, which claims the benefit of European Patent Application No. 11163329.3, filed on Apr. 21, 2011. These applications are hereby incorporated by reference herein.

FIELD OF THE INVENTION

The present invention relates to a device and a corresponding method for vital sign measurement of a person.

BACKGROUND OF THE INVENTION

It is nowadays possible to remotely measure vital signs, such as heart rate and respiration rate. Remote photoplethysmography (RPPG) measures small brightness variation of the skin using reflected ambient light. Respiration measurement is based on detection of motion and differences between video frames.

Within Ambient Healing Environments (AHE), the patient is presented with an audiovisual theme to assist in relaxing, for instance before or during an MRI or PET-CT scanning procedure. Remote (camera based) vital signs monitoring is susceptible to changes in the environment, notably the ambient lighting conditions. Within Ambient Healing Environments the environment is under full control, showing a comforting (visual or audiovisual) theme using video projection, light effects and/or sounds.

WO 2009/153700 A1 discloses a method of monitoring a vital parameter of a patient by measuring attenuation of light emitted onto tissue of the patient. In particular, a modulation scheme is disclosed for rejecting noise from ambient light.

US 2009/0299675 A1 discloses a system and a method for controlling a light emitting device for an optical sensor based on signal quality and/or power consumption requirements. Drive current and/or integration time is controlled as a function of detected ambient light or signal quality. As the signal quality decreases the drive current or integration time can be adjusted to provide a more usable signal. The method is particularly integrated in a fingerclip sensor.

However, there is currently no remote vital signs measurement equipment in the AHE, and there is also no connection between the vital signs measurement devices and ambience equipment.

SUMMARY OF THE INVENTION

It is an object of the present invention to provide a device and a corresponding method for vital sign measurement of a person enabling an accurate and reliable detection of vital signs of a person.

In a first aspect of the present invention a device for vital sign measurement of a person is presented comprising presentation means for presenting a person with an visual theme, illumination means for illuminating an illumination area, in which said person is located, whose vital signs shall be measured, optical measurements means for optically detecting optical detection signals from said illumination area, evaluation means for evaluating said optical detection signals and deriving a vital sign information from them, control means for controlling said illumination means to illuminate said illumination area allowing the detection of optical detection signal, from which a vital sign information can be derived despite changes of the visual theme.

In a further aspect of the present invention a corresponding method is presented.

Still further, in an aspect of the present invention a computer program is presented comprising program code means for causing a computer to carry out the steps of evaluating optical detection signals and deriving a vital sign information from them, and controlling said step of illuminating to illuminate said illumination area allowing the detection of optical detection signal, from which a vital sign information can be derived despite changes of the visual theme, when said computer program is carried out on the computer.

Preferred embodiments of the invention are defined in the dependent claims. It shall be understood that the claimed method and the claimed computer program have similar and/or identical preferred embodiments as the claimed device and as defined in the dependent claims.

The present invention is based on the idea to combine presentation means, e.g. an AHE, and vital sign measurement means and to control said illumination area in a way to guarantee minimum illumination conditions for vital sign measurements even if the presentation of a visual theme to the person changes. In this context, "illumination conditions" may be understood as conditions with respect to the emission of light from the illumination means including conditions with respect to color, texture, brightness, angle of lights, etc. One or more of the parameters relevant for controlling these conditions are controlled according to the present invention by the control means, e.g. implemented in a controller or programmed processor, included in the proposed device.

In an embodiment said control means is configured to control said presentation means to provide a visual theme in a way that does not prevent the detection of optical detection signals allowing deriving vital signal information from them, in particular to provide a visual theme having changes at a speed outside of the range of the detection of optical detection signals. This shall particularly avoid that the changes of the light effects of the visual theme interfere with the change rate of the vital signs such as heart rate or respiration rate, which would result in a decrease of the measurement accuracy.

In another embodiment said control means is configured to control said illumination means and/or said presentation means based on a feedback from said evaluation means. Thus, based on the feedback the illumination and/or the presentation of the visual theme can be appropriately influenced, e.g. in case of decreasing measurement accuracy to increase the accuracy again by providing better illumination conditions for the desired measurement of vital signs.

Preferably, said control means is configured to control said illumination means and/or said presentation means based on a quality indicator indicating the quality of the vital sign information and/or the derivation of said vital sign information from said optical detection signals.

In an embodiment the proposed device comprises a remote photoplethysmography (RPPG) device including said optical detection means and said evaluation means, wherein said evaluation means is configured to derive a PPG (photoplethysmography) signal as said vital sign information from said optical detection signals. RPPG is generally known. Such a method to measure skin color variations is described in Wim Verkruysse, Lars O. Svaasand, and J. Stuart Nelson, "Remote plethysmographic imaging using ambient light", Optics Express, Vol. 16, No. 26, December 2008. It is based on the principle that temporal variations in blood volume in the skin lead to variations in light absorptions by the skin. Such variations can be registered by a video camera that takes images of a skin area, e.g. the face, while processing calculates the pixel average over a manually selected region (typically part of the cheek in this system). By looking at periodic variations of this average signal, the heart beat rate and respiratory rate can be extracted. Such an RPPG device can be used in a device according to the present invention for measuring vital signs.

It has been found that RPPG signal amplitude is largest in green and infrared wavelengths. A second color channel is therefore proposed in another embodiment as a reference signal, where there is no influence from PPG (blue and red wavelengths). The illumination means is then preferably adapted to ensure that the illumination area is constantly illuminated with a suitable mix of wavelengths. Additionally, light effects should not change in same tempo as heart rate.

The RPPG amplitude is generally determined by the absorption spectrum of (de-)oxyhemoglobin. The optimal wavelengths are e.g. known from fingerclip sensors.

While in one embodiment the illumination area is constantly illuminated, in another embodiment said control means is configured to control said illumination means and said presentation means to alternately illuminate said illumination area and present said visual theme and to control said optical detection means to detect optical detection signals only when said illumination area is illuminated. Thus, the illumination can be optimized for the detection of optical detection signal for optimum vital sign measurement.

Further, said control means is preferably configured to control the percentage of the time during which the illumination means illuminates said illumination area and said optical detection means detects optical detection signals. This is preferably advantageous if the illumination light and the visual them are "conflicting", e.g. leading to a bad visual impression for the user, in which case the time during which the illumination means illuminates the illumination area is minimized.

Preferably, said control means is configured to control said illumination means to compensate for changes in illumination by the presentation of the visual theme, in particular for changes in brightness and/or color. Thus, the illumination, in particular the brightness and color, can be modified such that despite potentially negative changes of brightness and color of the visual theme, the measurement of vital signs is still possible with sufficient accuracy.

In another embodiment said evaluation means is configured to derive a respiration rate and/or a respiration depth of said person from said optical detection signals.

Respiration is generally detected using small frame-to-frame changes in a video sequence. To detect such small changes, the subject should have some surface contrast. Thus, it is proposed that the illumination means ensures that there is sufficient contrast. Contrast can e.g. be created by adjusting the angle of incident light. Even on a uniformly colored surface (e.g. a blanket) small shadows will appear if a point source is illuminating the surface at an angle.

In still another embodiment the proposed device further comprises correction means for correcting said optical detection signals to correct for changes of the visual theme, in particular per complete illumination area or sub-areas thereof. Thus, particularly changes of color and/or brightness of the visual theme are corrected per whole image, image areas or even per pixel. Additionally, direct light (e.g. from the visual theme) and indirect light (from ambience or reflections of the visual theme) are preferably corrected.

Said presentation means preferably includes an ambient healing equipment for presenting a person with an audiovisual theme. Such an ambient healing equipment, e.g. as particularly used in ambient healing environments (AHE), is generally known and e.g. described in "Ambient Experience helps soothe patients for successful scans", FieldStrength, published by the applicant, Issue 42, December 2010. Such an ambient healing equipment may, for instance, comprise lighting elements and/or displays which can provide different visual impressions to a patient, e.g. by completely coloring one or more walls of the room and/or by displaying pictures or textures on one or more walls or screens.

The illumination means may include a point light source, in particular an LED for emitting visual or infrared light. This enables, compared to the use of a large diffuse illuminator, to create sharply defined shadows to enhance the measurement of respiration rate and/or a respiration depth as mentioned above. When the person breathes, any shadows and surface texture will change in received image, i.e. the optical detection signals. These changes are then used for the vital sign measurement.

In an embodiment said illumination means includes at least two light sources for separately illuminating illumination sub-areas of said illumination area, wherein said control unit is configured to individually control said at least two light sources, wherein a light source is only controlled if a person is present in the associated illumination sub-area. For this detection, a RPPG signal, a respiration signal and/or any other detection, such as a motion detection by use of a known motion detector (e.g. a movement sensor).

BRIEF DESCRIPTION OF THE DRAWINGS

These and other aspects of the invention will be apparent from and elucidated with reference to the embodiment(s) described hereinafter. In the following drawing

DETAILED DESCRIPTION OF THE INVENTION

Figure 1:
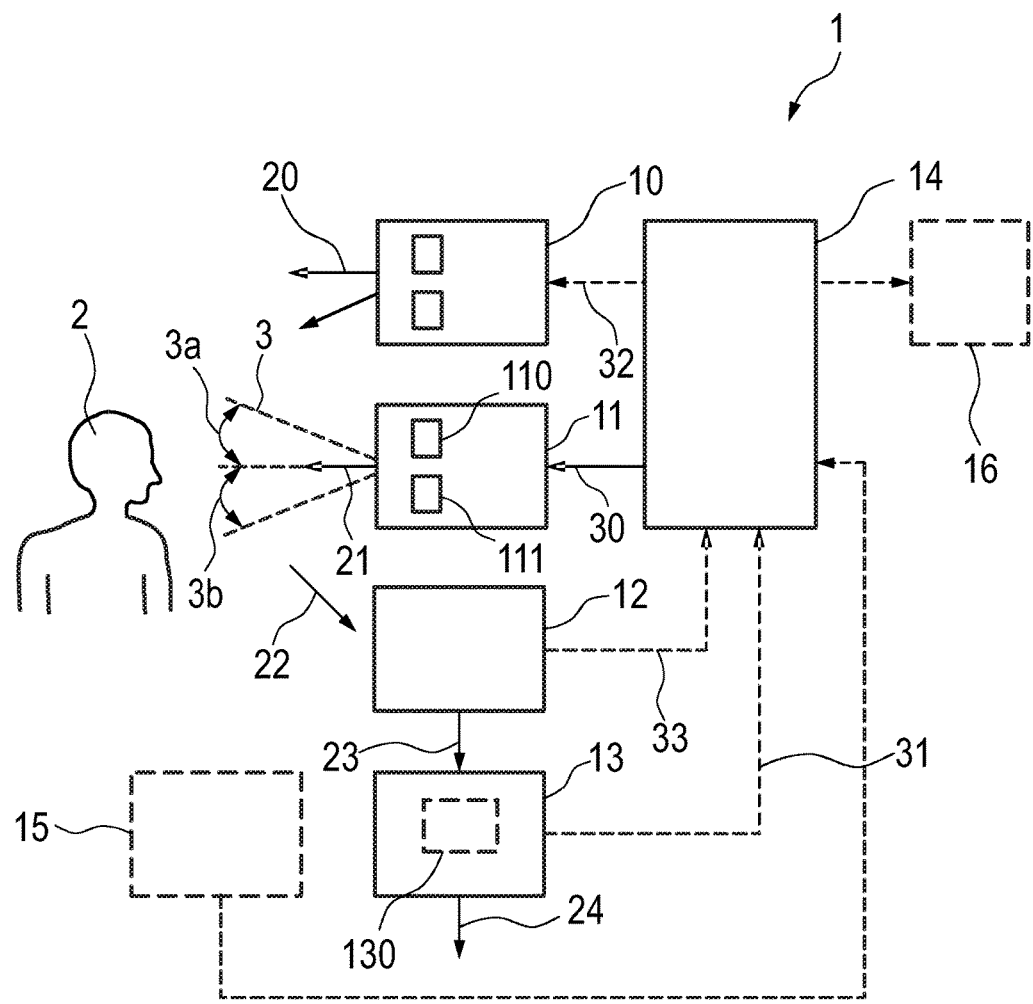
FIG. 1 shows a block diagram of an embodiment with several variations of a device according to the present invention.

FIG. 1 shows a block diagram of an embodiment of a proposed device 1 for vital sign measurement of a person 2 according to the present invention. FIG. 1 particularly shows an embodiment with essential elements, but also depicts further variants with various optional elements as will be explained below. The essential and optional elements can generally be arbitrarily combined in several different embodiments.

The device 1 comprises a presentation means 10 for presenting the person 2 with a visual or audiovisual theme 20. The presentation means 10 may be part of an ambient healing environments (AHE) for presenting visual or audiovisual themes 20 to persons and may e.g. include a video or image projection apparatus, a TV set or a beamer.

Further, the device 1 comprises an illumination means 11 for illuminating an illumination area 3, in which said person 2 is located, whose vital signs shall be measured, i.e. for directing an illumination signal 21 (e.g. visual light or infrared light) to the person 2. The illumination means 11 may e.g. include one or more controllable light units such as one or more LEDs or LED assemblies.

For optically detecting optical detection signals 23 from said illumination area 3 the device 1 comprises optical measurements means 12, e.g. including one or more photo diodes, an image sensor or a video camera, for measuring light 22 from said illumination area 3, from which the optical detection signals 23 are generated.

The detected optical detection signals 23 are evaluated by evaluation means 13, from which the desired vital sign information 24 is derived. The evaluation means 13 may e.g. include an evaluation unit as commonly provided in a RPPG device, by which a heartbeat signal of a person can be derived from optical detection signals, in particular video images of the skin (e.g. the cheeks) of the person.

For controlling said illumination means 11 via a control line 30 to illuminate said illumination area 3 allowing the detection of optical detection signal 23, from which the desired vital sign information 24 can be derived despite changes of the visual theme 20, control means 14 are provided. Said control means 14 may be implemented by a dedicated controller or by an appropriately programmed processor. Furthermore, also the evaluation means 13 can be implemented as a programmed processor, either separate from or integrated with the control means 14.

In an embodiment said illumination means 11 provides a constant illumination of the illumination area 3 (also called measurement area), e.g. a patient table, independent from theme setting. The constant light of the illumination means 11 may be in infrared wavelengths so that it does not interfere with visual stimuli.

Alternatively, the light in at least the illumination area 3 is alternating rapidly (e.g. at 100 Hz) between a setting optimized for measurement, and a complementary setting adding the theme colors. For instance, if the measurement requires only green light, and the theme requires white light, the light will alternate between green and magenta. Visibly, there will be no or very little difference to a human observer. However, a measurement system (i.e. the optical detection means) that is synchronized to the light can easily distinguish between the settings.

In case the measurement and theme conditions are conflicting, the visual impact can be minimized by measuring for only a small percentage of the time (e.g. a 10% duty cycle), i.e. the presentation means 10 and the illumination means 11 are controlled accordingly by the control means 14.

The device 1 may cycle through multiple measurement settings (e.g. one for heart rate, a second for respiration rated (SpO$_2$) in addition to the visual themes.

In an embodiment the optical detection signals 23, e.g. a video image, presented to the evaluation means 13, i.e. the vital signs detection, is compensated for changes in illumination from the presentation means 10. The brightness and color of the video image are corrected for direct and/or indirect illumination (reflections) from the ambient theme, preferably for both direct and indirect illumination. This can e.g. be implemented in (optional) corrections means 130, preferably included in the evaluation means 13.

There can be a single correction for the entire image or a correction per image area or even per pixel. The correction factors can be pre-computed when the AHE system is installed, via a so-called 'dark room calibration', whereby the contribution of each lamp is measured individually.

If the theme consists of predetermined content, the illumination effect can be recorded, and played back synchronously along with the theme.

Preferably, in an embodiment the (audio-)visual themes are optimized (preferably offline) to have only changes at a speed that falls outside of vital signs measurement range, preferably much slower. This allows the evaluation means 13 to filter out any changes due to the theme content.

A diffuse light source used as illumination means 11 may create insufficient contrast (shadows) for respiration sensing. Hence, in an embodiment the device 1 employs a point source light to create sharply defined shadows. The point source is preferably an infra-red LED.

Within certain rooms in the hospital (e.g. PET uptake room and patient ward), the patients are covered with a blanket as to maintain a constant body temperature. However, the blanket could interfere with respiration sensing. The measurement can be aided by using blankets with visible pattern to assist respiration sensing. In combination with an infrared sensitive camera, the pattern may be visible only in infrared wavelengths.

In an embodiment the (audio-)visual theme is adapted using feedback from vital signs measurement, i.e. there is optionally a feedback loop 31 from the evaluation means 13 to the control means 14 which accordingly controls the presentation means 10 via optional control line 32 so that the theme does not interfere with measurements (i.e., vital sign measurements). For example, changes in the light effects can be sped up or slowed down to a rate that does not overlap with the heart rate and respiration rate, respectively.

Additionally, measurement quality indicators, such as signal to noise ratio, generated by the optical detection means 12 or the evaluation means 13 and provided to the control means 14 by feedback loop 31 or feedback loop 33, can be used by the control means 14 via control line 32 to modify the theme (i.e., via the presentation means 10), e.g. by dimming the lights only to a point where measurement quality (i.e., vital sign measurement quality) is sufficient. This prevents measurement problems, for instance with dark-skinned patients, where an RPPG signal amplitude is lower.

Preferably, in an embodiment the illumination means 11 includes multiple (at least two) light sources 110, 111 that provide the constant or alternating light (as described above) at several illumination sub-areas 3a, 3b. However, the light setting in an illumination sub-area 3a, 3b is only adapted when a person (i.e. a vital sign) is present in that illumination sub-area 3a, 3b. The identification of a person in the illumination sub-area 3a, 3b may be based on "polling" for a vital sign information 24, e.g. a RPPG or respiration signal (e.g. once every minute) and/or by other (optional) detection means 15, such as motion detection means.

In an embodiment the device 1 comprises a signaling unit 16 to give a visual and/or auditory warning to the staff when presence is detected in the illumination area 3, but no vital sign can be measured within a predetermined interval. This either indicates a problem with the measurement (e.g. no skin visible resulting in no RPPG signal), or a problem with the patient (e.g. apnoea, heart failure).

The present invention can be implement in various devices and methods, including particularly ambient healing environments (e.g. for MRI and PET/CT), ambient relaxation environments for home use, patient monitoring, vital signs measurement (e.g. for fitness gyms), security systems (e.g. coupled to lights), etc.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A vital sign measurement device, the device comprising:
    presentation means for presenting a visual theme within an illumination area of a room to create an ambient healing environment (AHE) of illumination effects for a person located within the illumination area of the room, wherein the AHE comprises direct light from the illumination effects presented to the person and indirect light from reflections of the illumination effects presented to the person on one or more walls or screens in the room, wherein the illumination effects of the visual theme are in accordance with a predetermined ambience for the AHE in the room;
    illumination means for illuminating the illumination area of the room that includes the AHE, independent from the visual theme, with illumination conditions for vital sign measurements;
    optical measurement means for optically detecting optical detection signals from within said illumination area of the room that includes the AHE;
    evaluation means for evaluating said optical detection signals and deriving vital sign information of the person located within the illumination area of the room from the evaluated optical detection signals; and
    control means, responsive to feedback from said optical measurement means and said evaluation means, for controlling said illumination means to illuminate said illumination area of the room that includes the AHE to guarantee at least minimum illumination conditions for allowing the detection of optical detection signals from within said illumination area of the room that includes the AHE, from which a predetermined measurement accuracy of the vital sign information of the person can be derived, and further for controlling said presentation means to avoid changes rates in illumination effects of the visual theme for the predetermined ambience for the AHE in the room that interfere with a change rate of a vital sign of the vital sign information being derived from the evaluated optical detection signals.

2. The device as claimed in claim 1, wherein said control means is further configured to control said presentation means to provide the visual theme in a way that does not prevent the detection of optical detection signals allowing deriving vital signal information from them, wherein the visual theme includes changes in illumination effects at a speed outside of a range of the detection of optical detection signals.

3. The device as claimed in claim 1, wherein said control means is further configured to control one or more of said illumination means and said presentation means based on the predetermined measurement accuracy indicating a quality of one or more of the vital sign information and the derivation of said vital sign information from said optical detection signals.

4. The device as claimed in claim 1, wherein said optical measurement means and said evaluation means together comprise a remote photoplethysmography (PPG) device, wherein said evaluation means is configured to derive a PPG signal as said vital sign information from said optical detection signals.

5. The device as claimed in claim 1, wherein said control means is configured (i) to control said illumination means and said presentation means to alternately illuminate said illumination area via said illumination means and present said visual theme via said presentation means, and (ii) to control said optical measurement means to detect optical detection signals only when said illumination area is illuminated via said illumination means.

6. The device as claimed in claim 5, wherein said control means is further configured to control a percentage of time during which the illumination means illuminates said illumination area and said optical measurement means detects optical detection signals.

7. The device as claimed in claim 1, wherein said control means is configured to control said illumination means to compensate for changes in illumination effects by the presentation of the visual theme, wherein the changes in illumination effects include changes in one or more of brightness and color.

8. The device as claimed in claim 1, wherein said evaluation means is configured to derive one or more of a respiration rate and a respiration depth of said person from said optical detection signals.

9. The device as claimed in claim 1, further comprising correction means for correcting said optical detection signals to correct for changes in illumination effects of the visual theme per complete illumination area or sub-areas thereof.

10. The device as claimed in claim 1, wherein said presentation means comprises an ambient healing equipment for presenting an audiovisual theme proximate or within the illumination area.

11. The device as claimed in claim 1, wherein said illumination means comprises a point light source, wherein the point light source includes an LED for emitting visual or infrared light.

12. The device as claimed in claim 1, wherein said illumination means includes at least two light sources for separately illuminating illumination sub-areas of said illumination area, and
    wherein said control unit is configured to individually control said at least two light sources, wherein a light source of said at least two light sources is only switched on in response to a detection of a person present in the associated illumination sub-area.

13. A method for vital sign measurement, the method comprising the steps of:
    presenting a visual theme within an illumination area of a room to create an ambient healing environment (AHE) of illumination effects for a person located within the illumination area of the room, wherein the AHE comprises direct light from the illumination effects presented to the person and indirect light from reflections of the illumination effects presented to the person of on one or more walls or screens in the room, wherein the illumination effects of the visual theme are in accordance with a predetermined ambience for the AHE in the room;

illuminating the illumination area of the room that includes the AHE, independent from the visual theme, with illumination conditions for vital sign measurements;

optically detecting optical detection signals from within said illumination area of the room that includes the AHE;

evaluating said optical detection signals and deriving vital sign information of the person located within the illumination area of the room from the evaluated optical detection signals; and controlling, in response to feedback from the optically detecting and evaluating steps, said step of illuminating to illuminate said illumination area of the room that includes the AHE to guarantee at least minimum illumination conditions for allowing the detection of optical detection signals from within said illumination area of the room that includes the AHE, from which a predetermined measurement accuracy of the vital sign information of the person can be derived, and further controlling said step of presenting to avoid changes rates in illumination effects of the visual theme for the predetermined ambience for the AHE in the room that interfere with a change rate of a vital sign of the vital sign information being derived from the evaluated optical detection signals.

14. A non-transitory computer readable medium embodied with a computer program comprising program code for causing a computer to carry out the steps of evaluating and controlling of the method as claimed in claim 13 when said computer program is carried out on the computer.

15. The method of claim 13, wherein said controlling step further comprises controlling one or more of illuminating and presenting steps based on the predetermined measurement accuracy indicating a quality of one or more of the vital sign information and the derivation of said vital sign information from said optical detection signals.

* * * * *